United States Patent [19]

Komatsu et al.

[11] Patent Number: 4,817,050

[45] Date of Patent: Mar. 28, 1989

[54] DATABASE SYSTEM

[75] Inventors: Kenichi Komatsu, Tochigi; Kiyoshi Tawara, Ootawara; Eitaro Nishihara, Ootawara; Seiji Fujimoto, Ootawara, all of Japan

[73] Assignee: Kabushiki Kaisha Toshiba, Kawasaki, Japan

[21] Appl. No.: 933,400

[22] Filed: Nov. 21, 1986

[30] Foreign Application Priority Data

Nov. 22, 1985 [JP] Japan ................. 60-261286
Jan. 28, 1986 [JP] Japan ................. 61-14633

[51] Int. Cl.⁴ .................. G06K 9/00; H04N 1/10; G06F 15/40
[52] U.S. Cl. .................. 364/900; 358/260; 358/280; 358/257; 364/518; 382/65
[58] Field of Search ... 364/200 MS File, 900 MS File, 364/518; 358/293, 335, 280, 256, 290; 340/721; 382/65, 41

[56] References Cited

U.S. PATENT DOCUMENTS

| 4,555,803 | 11/1985 | Hirose | 358/335 |
| 4,571,700 | 2/1986 | Emry, Jr. et al. | 364/900 |
| 4,587,635 | 5/1986 | Hashimoto et al. | 364/900 |
| 4,601,003 | 7/1986 | Yoneyama et al. | 364/900 |
| 4,607,290 | 8/1986 | Murakami | 358/260 |
| 4,653,021 | 3/1987 | Takagi | 364/900 |
| 4,658,299 | 4/1987 | Tanaka et al. | 358/293 |
| 4,661,988 | 4/1987 | Shimizu | 340/721 |
| 4,674,064 | 6/1987 | Vaughn | 364/900 |
| 4,695,895 | 9/1987 | Nagashima | 358/280 |
| 4,695,975 | 9/1987 | Berdry | 364/900 |
| 4,758,980 | 7/1988 | Tsunekawa et al. | 382/61 |
| 4,760,458 | 7/1988 | Watanabe et al. | 358/256 |
| 4,768,099 | 8/1988 | Mukai | 358/256 |

Primary Examiner—Thomas M. Heckler
Assistant Examiner—Viet Q. NGuyen
Attorney, Agent, or Firm—Oblon, Fisher, Spivak, McClelland & Maier

[57] ABSTRACT

A database system is provided in a network system capable of exchanging medical data, including at least image data and key data associated therewith, and can store and retrieve the medical data via the network system. The database system has first and second data file devices and a file management device. The first data file device stores image data supplied via the network system in a first rewritable storage. The second data file device stores image data transferred from the first storage in a non-rewritable second storage. The file management device has an index data storage for storing the key data, supplied via the network system, and memory addresses of image data, which correspond to the key data, on the first and second storages in correspondence with each other, and manages storing and reading of the image data in and from the first and second data file devices.

21 Claims, 10 Drawing Sheets

FIG. 3

| ADDRESS | DATA | | | |
|---|---|---|---|---|
| 001 | IMAGE 1 | ADDITIONAL 1 | | |
| 002 | IMAGE 2 | IMAGE 3 | ADDITIONAL 2 | |
| 003 | TEXT 1 | | | |
| 004 | IMAGE 4 | ADDITIONAL 3 | | |
| 005 | | | | |
| 006 | IMAGE 5 | ADDITIONAL 4 | TEXT 2 | |
| 007 | IMAGE 6 | ADDITIONAL 5 | | |
| 008 | IMAGE 7 | ADDITIONAL 6 | | |
| 009 | IMAGE 8 | IMAGE 9 | ADDITIONAL 7 | |
| 010 | TEXT 3 | | | |
| 011 | TEXT 4 | | | |

| ADDRESS 50 | KEY 51 | TYPE 52 | LENGTH 53 | IDENTIFICATION CODE 54 |
|---|---|---|---|---|
| 001 | WHO | 1 | -- | 8407 |
| 002 | UCG | 3 | -- | 6210 |
| 003 | CCU | 10 | -- | 90A0 |
| 004 | WHO | 1 | -- | 11PM |
| 005 | | | | |
| 006 | WPW | 18 | -- | 2537 |
| 007 | DNA | 1 | -- | C271 |
| 008 | WHO | 1 | -- | 1985 |
| 009 | UCG | 3 | -- | 007 |
| 010 | ICU | 10 | -- | 1248 |
| 011 | ALS | 10 | -- | AIDS |
| | | | | |

FIG. 9

151 — IMAGE ADDRESS

152 — KEY DATA

| TYPE OF FILE | FILE NUMBER | ADDRESS | PATIENT'S NUMBER | PATIENT'S NAME | SEX | AGE | DATE OF BIRTH | OUTPATIENT / INPATIENT | BED |
|---|---|---|---|---|---|---|---|---|---|
| 9 | 99 | 9999 | 9(8) | X(25) | 9 | 999 | 9(8) | 9 | 99×99 |
| 153 | 154 | 155 | 156 | 157 | 158 | 159 | 160 | 161 | 162 |

152 — KEY DATA

| EXAMINATION DATE | PORTION | METHOD | CONDITION | LABORATORY NUMBER | DIAGNOSTIC RESULT | RELIABILITY | CODE OF DOCTOR IN CHARGE OF DIAGNOSIS | EXAMINATION SYSTEM | SYSTEM NUMBER |
|---|---|---|---|---|---|---|---|---|---|
| 9(8) | X(12) | X(12) | X(20) | 99 | X(20) | 99 | 9(8) | X(12) | 999 |
| 163 | 164 | 165 | 166 | 167 | 168 | 169 | 170 | 171 | 172 |

150

DATABASE SYSTEM

BACKGROUND OF THE INVENTION

The present invention relates to a database system which can file image data through a network system and, more particularly, to a database system for storing medical data including image data such as diagnostic images.

In a database system using a network system, a plurality of nodes of a network system are connected to one or a plurality of data output devices, database systems, and terminals. The data output devices output data to be stored, e.g., image data. The output data is filed in the database. The data filed in the database is retrieved by the terminals.

A practical example of a database system using a network system will be described with reference to FIG. 1. This database system handles, e.g., image data.

The network system shown in FIG. 1 is a loop-like link-type network system. Loop-like common data transmission path 400 is provided with a plurality of nodes 401, 402, 403, 404, and 405. Data, i.e., image data is transferred among nodes 401 to 405 via transmission path 400. In image data transfer, image data to be stored, additional data of the image data, and a procedure signal for allowing data exchange are exchanged.

In the network system having the above arrangement, node 401 is connected to image data generator 406 as a data output device and data generated by generator 406 is output onto transmission path 400. The output data is filed by database system 407 connected to node 402. Database system 407 accumulates image data from generator 406 as an image database. The data stored in database system 407 is retrieved by terminal 408 connected to node 403 and is transferred thereto.

Database system 407 has a memory device for storing data, e.g., a rewritable storage (a so-called erasable storage) such as a semiconductor memory device, a magnetic tape device, and a magnetic disk device, or a non-rewritable storage (a so-called non-erasable storage) such as an optical disc device. In a general database system, either a rewritable storage or a non-rewritable storage is used. Particularly in a database system for storing image data, a memory device having a large memory capacity of several GB (gigabytes) is required. Therefore, a database system for storing image data uses a rewritable storage having a high recording density. An optical disc device requires, however, a long access time of 800 msec to access stored image data while a recording density per optical disc is as high as 3.6 GB. Generally, the larger the memory capacity of a memory device, the longer an average access time required for data to be read out from the memory device. As a result, if a memory device has a large memory capacity, a retrieval time required for the memory content is prolonged in proportion to the access time.

Furthermore, when a non-rewritable storage has written data on its recording medium, it cannot write other data on the same location of the recording medium.

Thus, when the image data is edited, the image before editing is left without being erased, and the amount of data to be stored is further increased.

In this manner, in a conventional database system, when a large amount of data, such as image data, is to be handled, since a considerably large amount of data is stored in a memory device, the memory device must have a large memory capacity while the access time is prolonged, degrading processing efficiency.

Particularly when a medical database system is to be constituted, most of the data used for medical diagnosis, examination, or therapy is image data having a high density and covering a broad range of gradation, e.g., a CT (computed tomographic) image and an MR (magnetic resonance) image. Therefore, a memory device must have a still larger memory capacity while the access time is further prolonged, thus degrading the processing efficiency.

SUMMARY OF THE INVENTION

It is an object of the present invention to provide a database system whose processing efficiency is improved.

The database system according to the present invention has first and second data file devices and a file management device is provided in a network system capable of exchanging medical data, including at least image data and key data associated thereto, and can store and retrieve the medical data via the network system. The first data file device stores image data supplied via the network system in a rewritable first storage. The second data file device stores image data transferred from the first storage in a non-rewritable second storage. The file management device has an index data storage for storing the key data, supplied via the network system, and memory addresses of image data, which correspond to the key data, on the first and second storages in correspondence with each other, and manages storing and reading of the image data in and from the first and second data file devices.

According to the database system of the present invention, data which is used relatively frequently is stored in the rewritable storage and data which is used relatively less frequently is stored in the non-rewritable storage. As a result, the processing efficiency of the database system is improved.

BRIEF DESCRIPTION OF THE DRAWINGS

FIG. 3 shows a memory format of a memory module of the system shown in FIG. 2;

FIGS. 9 and 10 show format of the index file of the system shown in FIG. 8, respectively;

DETAILED DESCRIPTION OF THE PREFERRED EMBODIMENTS

Figure 1:
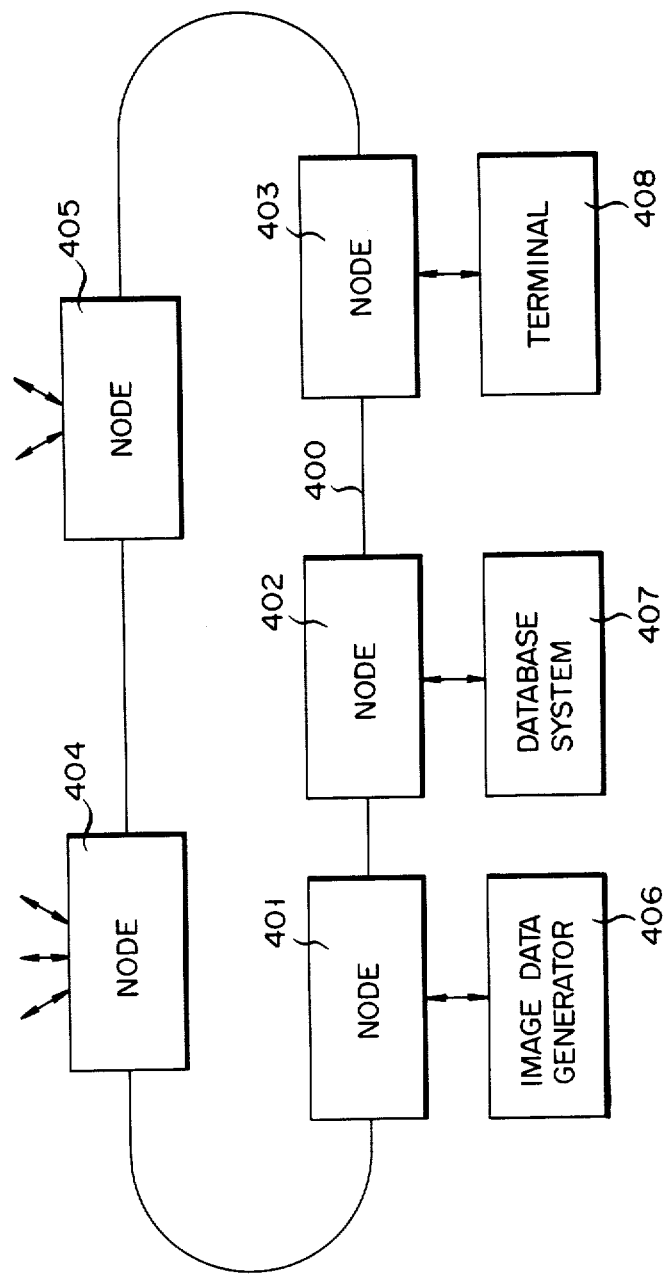
FIG. 1 is a block diagram of an example of a network system including a general image database system.

A database system according to a first embodiment of the present invention will be described with reference to FIG. 2. The database system shown in FIG. 2 is connected to a network system in the same manner as database system shown in FIG. 1.

Node 5 is connected to common data transmission path 4. Image data from an image data generator connected to another node (not shown), additional data of the image data, and a command or status data for data transfer are supplied to node 5 via transmission path 4. The image data generator is a device for supplying image data onto transmission path 4, such as an image recording/reproducing system, an image pick-up system, a copy system, a diagnostic system (e.g., a computed tomography system or a magnetic resonance imaging system) for generating image data. Node 5 supplies image data and additional data to another node (not shown) connected to a terminal (not shown) via transmission path 4.

Figure 2:
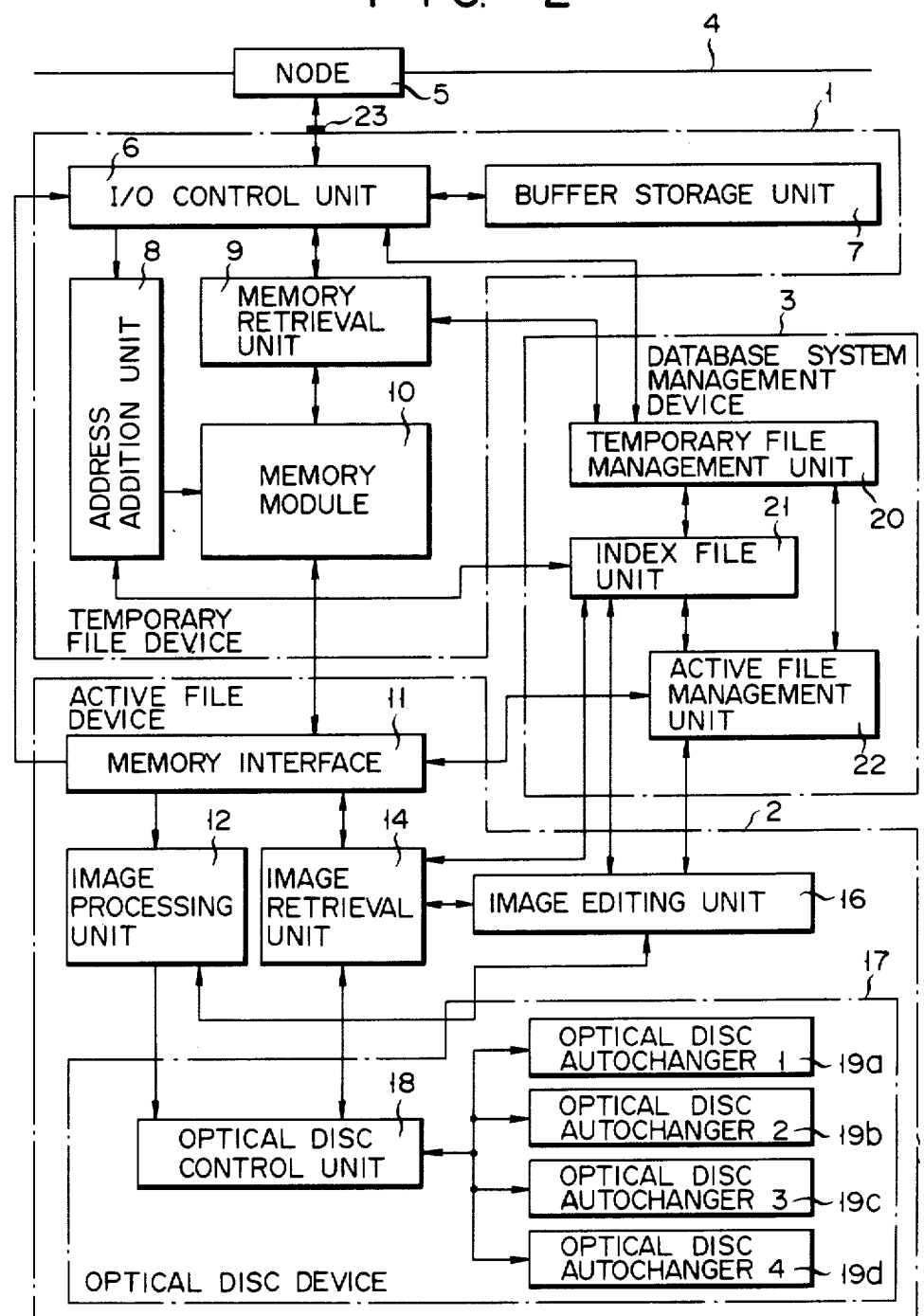
FIG. 2 is a block diagram of a database system according to a first embodiment of the present invention.

The database system shown in FIG. 2 is constituted by temporary file device 1, active file device 2, and system management device 3.

Temporary file device 1 has I/O (input/output) control unit 6, buffer storage unit 7, address addition unit 8, memory retrieval unit 9, and memory module 10.

Active file device 2 has memory interface 11, image processing unit 12, image retrieval unit 14, image editing unit 16, and optical disc device 17. Disc device 17 has optical disc control unit 18 and optical disc autochangers 19a to 19d.

System management device 3 has temporary file management unit 20, index file unit 21, and active file management unit 22.

Data exchange between node 5 and file device 1 is performed via coupling 23. More specifically, coupling 23 corresponds to a data transmission section between the network system and the database system. Coupling 23 can thus couple remote two points through a beam or radiowave.

I/O control unit 6 of file device 1 is connected to node 5 via coupling 23. Control unit 6 is connected to buffer storage unit 7 which can store a plurality of data. Memory retrieval and address addition units 9 and 8 are also connected to control unit 6. Memory module 10 is connected to both units 9 and 8.

Memory module 10 is connected to file device 2. Data exchange is performed between module 10 and file device 2.

Memory interface 11 of file device 2 is connected to both memory module 10 and active file management unit 22 of database system management device 3. Memory interface 11 is also connected to both image processing unit 12 and image retrieval unit 14. Interface 11 is also connected to I/O control unit 6 of file device 1. Units 14 and 12 are connected to image editing unit 16 and to optical disc control unit 18 of optical disc device 17. Control unit 18 is connected to four optical disc autochangers 19a to 19d. Autochangers 19a to 19d each store a plurality of optical discs. A desired optical disc is selected by control unit 18 and is subjected to recording or reproduction.

System management device 3 manages temporary and active file devices 1 and 2. Management device 3 aids operation of file devices 1 and 2 and is provided for allowing smooth data transmission therebetween. Temporary file management unit 20 of management device 3 is connected to both I/O control and memory retrieval units 6 and 9. Index file unit 21 is connected to management, address addition, image retrieval, and image editing units 20, 8, 14, and 16. Management unit 22 is connected to index file, temporary file management, and image editing units 21, 20, and 16.

Temporary file management unit 20 employs a description system divided into three hierarchical stages of external schema for describing a data structure with an expression suitable for a particular application, internal schema for describing a physical structure of a database and data internal expression, and conceptual schema, located between the internal and external schemas, for matching them. The schema of each stage is described with a predetermined data description language (DDL). In this case, a data dictionary is prepared and data of each schema is transformed using the function of the data dictionary, so that interface between a terminal and memory module 10 can be achieved.

The operation of the database system having the above arrangement will be described for cases wherein: (1) image data from common data transmission path 4 is stored in memory module 10; (2) data stored in module 10 is retrieved; (3) data in module 10 is transferred to optical disc device 17 and is stored therein; and (4) data stored in optical disc device 17 is read out and is transferred to a terminal.

(1) When image data from common data transmission path is stored in memory module Data to be stored is supplied from an image data generator to I/O control unit 6 via common data transmission path 4 and node 5. When the data is supplied from node 5, if temporary file device 1 is processing another instruction, the data is temporarily stored in buffer storage unit 7. When processing of the other instruction is ended, the data temporarily stored in storage unit 7 is read out and transferred to address addition unit 8. If file device 1 is not processing another instruction, the data is directly transferred to addition unit 8. Storage unit 7 comprises a rewritable storage, e.g., a RAM (random-access memory) and a hard disc device.

Address addition unit 8 adds address data supplied from index file unit 21 to the supplied data, and transfers it to memory module 10 to be stored therein. Thus, the data to be stored coincides with the address and hence the stored data can be read out by the address or be identified by the address.

Memory module 10 stores a plurality of images. For example, assuming that a 6-KB memory is required for storing a single-frame image, a memory capacity required for storing 1,000-frame image data is 60 MB (megabytes). Each image is assigned a corresponding address.

FIG. 3 schematically shows the memory content of memory module 10, which is an example of an image database file. The database file consists of address portion 40 and data portion 41. Each data of data portion 41 is assigned a corresponding address. For example, address "001" is added to certain one-frame image data 1 and additional data 1 added thereto. Additional data 1 represents, e.g., date and/or place image data 1 was picked up or generated, the name of a person in charge of handling image data 1 and/or a person as the object, error detection data, and so on. Continuous 2-frame image data 2 and 3 and additional data 2 thereof is stored at address "002". Text data 1, i.e., non-image data such as paragraph data or message data input by a wordprocessor, is stored at address "003". Data other than text, e.g., a program, can be stored. No data is stored at address "005" (data stored at this address is erased).

As memory module 10, a rewritable storage such as a magnetic bubble device, a CCD (charge coupled device), a magnetic disc device, and a magnetic tape device can be used. In this manner, since a rewritable storage is used as module 10 and data which is accessed comparatively frequently is constantly written in module 10, an access time required for retrieving data can be shortened.

Index file unit 21 has an index file for storing an address, type, length, and identification code of data stored in module 10, and key data. A rewritable storage requiring a short access time is preferably used as the index file.

Figures 4, 5:
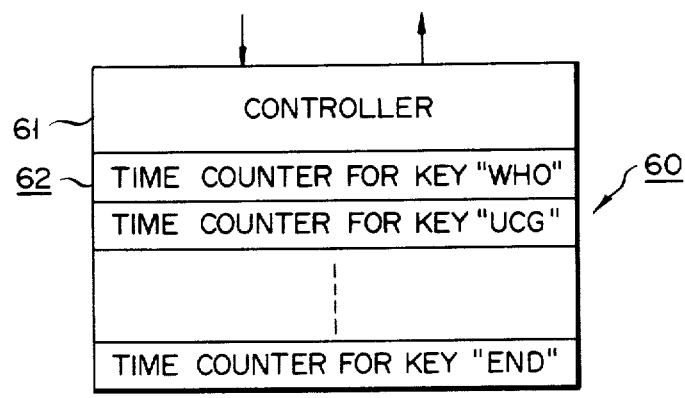
FIG. 4 shows a memory format of an index file of the system shown in FIG. 2.
FIG. 5 shows an arrangement of a time management device applied to the system shown in FIG. 2.

FIG. 4 shows an example of the content of the index file. The index file consists of address portion 50 storing address data the same as the address of the data stored in the database file, key portion 51 for storing key data, type portion 52 representing the type of data portion 41, length portion 53 representing the length of image data, additional data, and text data, and identification code portion 54. A hashing method is adopted for storing these data. More specifically, each data is directly edited in accordance with the hashing function, and is stored. The hashing function is a logical structure for storing data that enables high-speed retrieval of data constituting a large table. When the amount of data is small, a sequential arrangement structure of a memory structure using an index or pointer is adopted.

Data to be supplied in key and identification code portions 51 and 54 is supplied from a terminal. The data of remaining address, type, and length portions 50, 52, and 53 is calculated by temporary file management unit 20 and is automatically added to the data supplied from the terminal. Management unit 20 calculates data of address, type, and length portions 50, 52, and 53 so that it is efficiently stored in memory module 10. Key data to be stored in key portion 51 can be character data including an alphanumeric character and a special symbol. In FIG. 4, key data is constituted by three alphanumeric characters. Key data represents personal data on a person to be examined, such as the name, the name of the company, the position, the date of birth, and the year of employment at the company, data on the doctor in charge, such as the name, medical data such as the department (internal department, surgical department, etc.) and the name of the disease, or the type of data, such as CT image, MR image, electrocardiograph, and ultrasonic image. A plurality of key data can be used in a complex manner as the key data. The same key data can be assigned to a plurality of addresses in key portion 51. For example, key data "WHO" is assigned to addresses "001", "004", and "008", in FIG. 4. As a result, when "WHO" is accessed, all the addresses, types and lengths assigned with key "WHO" can be retrieved.

The data of type portion 52 represents the type of data stored in the database file. In FIGS. 3 and 4, type data "1" represents that the stored data is image data +additional data, and type data "3" represents that the stored data is image data +image data +additional data.

Identification code 54 is a specific code, e.g., a serial number, which is selected as a unique address. Data at each address can be retrieved from a terminal by code 54.

In the above case, the database file and the index file are separately arranged. However, both can be stored in memory module 10, or the index file can be stored in a database system connected to a node other than a node connected to the database file. A rewritable storage is used as the index file. Therefore, unnecessary data can be erased like data at address "005", and new data can be stored.

(2) When data stored in memory module is to be retrieved

A retrieval instruction and identification code data or key data are supplied from a terminal to I/O control unit 6 via common data transmission path 4 and node 5. When a retrieval instruction and identification code data or key data are supplied, if memory module 10 is used, the supplied data is temporarily stored in buffer storage unit 7. When processing using module 10 is ended, the instruction and identification code data or key data are fetched from storage unit 7 and are processed. Storage unit 7 can determine priority of processing instructions corresponding to the respective stored data. An urgent instruction is processed prior to the other ones.

When it is determined that a retrieval instruction is supplied, a retrieval instruction is supplied from control unit 6 to memory retrieval unit 9. Upon reception of this instruction, retrieval unit 9 checks whether data to be retrieved which corresponds to the key or identification code data is stored in index file unit 21 via temporary file management unit 20. If such data is present, address data corresponding to the key or identification code data, and type data are fetched from address and type portions 50 and 52 and are transferred to memory retrieval unit 9. When the key data corresponds to a plurality of addresses, all these addresses are transferred. Data stored in memory module 10 is retrieved by memory retrieval unit 9 in accordance with the address data. A retrieved image and text data are transferred to node 5 via control unit 6 and are transferred to the terminal via data transmission path 4.

(3) When data in memory module is stored in optical disc device

An "instruction requesting data transfer from memory module 10 to optical disc device 17" is supplied from a terminal to node 5 via common data transmission path 4. This instruction is transmitted from node 5 to I/O control unit 6. Upon reception of this instruction, control unit 6 supplies retrieval key data to memory retrieval and temporary file management units 9 and 20 in order to read data from module 10. In response to the key data, management unit 20 reads an address corresponding to the key data and the other data from the index file in index file unit 21. Image data and additional or message data are read out from module 10 in accordance with the readout address and the other data. In this case, when a single key is assigned to a plurality of addresses, data at all the assigned addresses are read out. The readout data is supplied to image processing unit 12 via memory interface 11 in active file device 2. When the data supplied to processing unit 12 is data corresponding to a plurality of data, it is supplied from processing unit 12 to image editing unit 16 and is edited. Examples of editing by editing unit 16 include collecting of images only and then adding text data such as a message, sequential sorting of data in accordance with the order at which they are stored in module 10, and sorting or combining of images in accordance with the type identification code and key data. Nonrequired data or overlapping data is deleted by editing unit 16. Data edited by editing unit 1 is returned to image processing unit 12 and supplied to optical disc control unit 18 of optical disc device 17. If only one address corresponding to the specified key is found, data is supplied from processing unit 12 directly to control unit 18 without going through editing unit 16.

Each of optical disc autochangers 19a to 19d of optical disc device 17 stores a plurality of non-erasable optical discs. One of the optical discs is selected and data supplied from processing unit 12 is written in it. In this case, since the optical disc is non-rewritable, when written data is to be updated, it must be invalidated, and new data must be written at a location different from that for the prior data.

Optical disc control unit 18 is connected to four autochangers 19a to 19d and manages the addresses at which respective data are stored. Optical disc device 17 has a memory capacity larger than that of memory module 10.

In this manner, all the data stored in temporary file device 1 can be transferred to (optical disc device 17 of) active file device 2. In other words, since data stored in file device 2 is data which is once stored in file device 1, an active file, i.e., optical disc device 17 having a larger memory capacity than that of the temporary file, i.e., memory module 10, is required.

In the above manner, an address corresponding to key data designated by the terminal is read out from the index file in accordance with the key data, and data stored at the corresponding address of memory module 10 is transferred to and stored in optical disc device 17. Note that in the above description the key data, stored in the index file and designated by the terminal, is data comprising a single key. However, a plurality of keys can be used instead. In this case, retrieval is performed using each of or an arbitrary combination of the keys. Alternatively, key data given by an algebraic equation can be used. Furthermore, the index file may be provided at any location as far as the database file can be read out. The data of the index file can be physically and/or functionally separate.

Another example of a case wherein data is transferred from module 10 to control unit 18 will be described.

In this example, time management unit 60 shown in FIG. 5 is provided so as to manage access to memory module 10 while accessing it (management unit 60 is, e.g., connected to an index file unit). In management unit 60, a time elapsed since each data is stored in module 10 is counted by time counter 62 in units of key data. More specifically, counter 62 is provided in units of keys and counts the number of clocks having a predetermined period. When data is stored, the counter of the corresponding key is reset. Accordingly, the count of each key corresponds to the time lapse since data is stored at that key. Controller 61 of management unit 60 controls time counter 62 to perform the above counting. When a predetermined period of time elapses and the count of a certain key of counter 62 has reached a predetermined value, unit 60 transfers data corresponding to the key from temporary file device 1 to active file device 2. Time management unit 60 manages time in units of the contents of key data. However, management unit 60 may manage time in units of identification codes or combinations of them. Basically, time management is performed in units of groups of image data that are associated with each other.

With management unit 60, data transfer from temporary file device 1 to active file device 2, hence to a terminal, can be performed automatically and appropriately. More specifically, management unit 60 transfers data concerning a key from memory module 10 to optical disc device 17 only when the data concerning the key is not accessed at all during a predetermined period of time. Conversely, when memory module 10 is accessed for a predetermined key during the predetermined period of time, management unit 60 sets a time counter corresponding to the key and repeats counting the time from the beginning. In this manner, data which is used frequently is stored in temporary file device 1.

When data transfer from module 10 to control unit 18 has been completed in the above manner, data in module 10 and index file unit 21 concerning the transferred data is cleared.

(4) When data in optical disc device is transferred to terminal

A retrieval instruction from a terminal is supplied to database system management device 3 via transmission path 4, node 5, and I/O control unit 6. The location of data to be retrieved is searched by temporary file management, active file management, and index file units 20, 22, and 21 of system management device 3. If the location is in optical disc device 17, a detailed location of the data to be retrieved is searched using image retrieval and optical disc control units 14 and 18. Searched data is read out from an optical disc (autochangers 19a to 19d) by optical disc control unit 18 and transferred to image retrieval unit 14. In this case, if the terminal requests image editing, image data is supplied to image editing unit 16, edited, and is returned to retrieval unit 14. The retrieved or edited data is transferred from retrieval unit 14 to the terminal via memory interface 11 and I/O control unit 6.

When data is transferred from a non-rewritable storage, e.g., optical disc device 17, to the terminal, data from disc device 17 may be directly transferred to common data transmission path 4 and at the same time to memory module 10 and stored. In this case, data having the same key as this data is also read out from disc device 17 and stored in module 10. Then, since an access time to module 10 is shorter than that to disc device 17, a retrieval time required for reading out the same data again from the terminal or data associated thereto is shortened. More specifically, when a rewritable storage is provided at an input/output section of a non-rewritable storage and data supplied from data transmission path 4 and accessed frequently is constantly stored in the rewritable storage, the user can obtain data more efficiently.

In the first embodiment, buffer storage unit 7 is provided. Therefore, in addition to the above effect, even when the database system is busy, data exchange can be performed with flexibility. Image editing unit 16 can remove overlapping data, thus increasing the memory capacity. If data is divisionally stored in optical disc device 17, it can be synthesized and reproduced. Furthermore, image data can be expanded or compressed and be supplied to the terminal.

A database system according to a second embodiment of the present invention will be described with reference to FIG. 6. The network system shown in FIG. 6 includes the database system of the present invention and is a link-type network system having two loop-like common data transmission paths 4-a and 4-b each having a plurality of nodes. Transmission paths 4-a and 4-b are connected via gateway 73. In this system, temporary file and active file devices as those of the system of the first embodiment are incorporated in a private branch communication system. The network system can be a bus-type, tree-type, or star-type network system, or a system using a combination thereof as a network. As common data transmission paths 4-a and 4-b, a transmission path having a dual-core or coaxial cable as a transmission medium, an optical fiber transmission path which performs communication using a beam of a semiconductor laser or a light-emitting diode, or a radio communication transmission path for satellite communication can be used. The network system is not limited to private branch communication, but can be a more global network system (e.g., public communication, submarine communication, international communication, or satellite communication).

Figure 6:
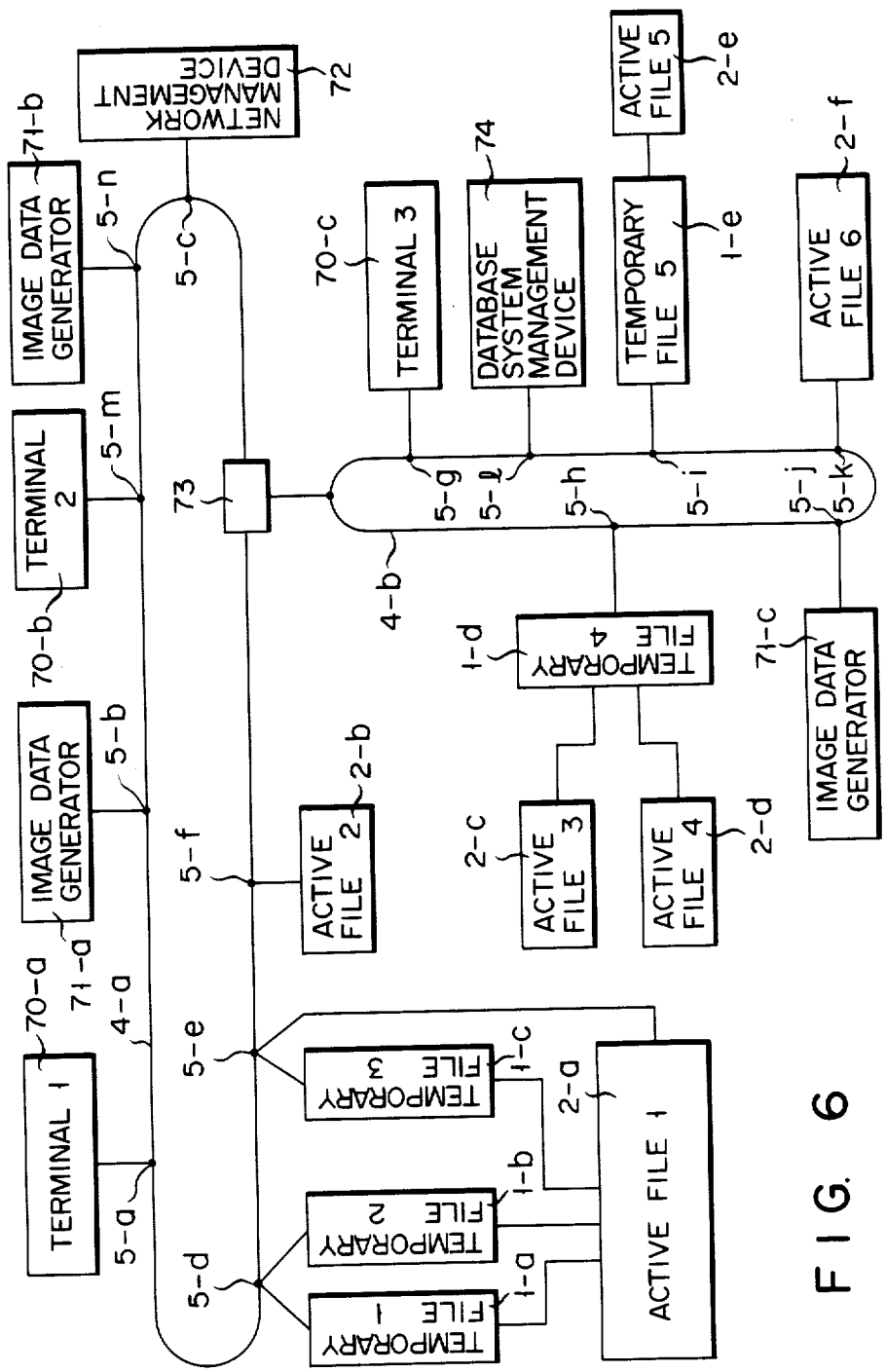
FIG. 6 is a block diagram of a network system including a database system according to a second embodiment of the present invention.

Common data transmission path 4-a shown in FIG. 6 is provided with nodes 5-a to 5-f, 5-m, and 5-n. Common data transmission path 4-b is provided with nodes 5-g to 5-k. Nodes 5-a, 5-m, and 5-g are connected to terminals 70-a to 70-c, respectively. Nodes 5-b, 5-n, and 5-j are connected to image data generators 71-a to 71-c, respectively. Node 5-d is connected to two temporary file devices 1-a and 1-b. Nodes 5-e, 5-h, and 5-i are connected to temporary file devices 1-c, 1-d, and 1-e, respectively. Nodes 5-k, 5-c, and 5-l are connected to active file device 2-f, network management device 72, and system management device 74, respectively.

Active file device 2-a has a storage of a large memory capacity (e.g., several hundreds of GB or more), and is connected to file devices 1-a to 1-c and node 5-e. It can be selected whether data read out from file data 2-a is directly transferred to transmission path 4-a or to transmission path 4-a via file device 1-a, 1-b, or 1-c. Also, file device 1-d is connected to both active file units 2-c and 2-d.

Gateway 73 appropriately performs exchange of protocol between a first network constituted by transmission path 4-a and a second network which is constituted by transmission path 4-b and performs data communication using a protocol different from that of the first network. Network management device 72 manages transmission path 4-a via node 5-c such that data exchange among nodes 5-a to 5-f, 5-m, and 5-n can be performed smoothly.

Temporary file devices 1-a to 1-e are distributed on data transmission paths 4-a and 4-b and store data obtained therefrom. Therefore, the amount of data handled by each temporary file device can be reduced, and the access time to temporary file devices 1-a to 1-e is shortened. In addition, even if trouble occurs in one file device, data can be read out from another file device (trouble in one file device does not disable the entire system). For the same reason, active file devices 2-a to 2-f are distributed and appropriately store data from temporary file devices 1-a to 1-e in a distributed manner. Since file device 2-a is connected to file devices 1-a to 1-c, it must have a larger memory capacity than their total memory capacity.

The operation of the system having the above arrangement will be described.

First, image data output from image data generators 71-a to 71-c is supplied to rewritable storages in temporary file devices 1-a to 1-e via nodes 5-b, 5-n, and 5-j, and common data transmission paths 4-a and 4-b. Key data associated with the image data output from devices 71-a to 71-c together with the image data is stored in the index file of system management device 74.

Subsequently, when arbitrary image data is to be transferred from a temporary file device to an active file device, key data is supplied from any one of terminals 70-a to 70-c to system management device 74. Management device 74 collates the key data with the data of the index file, and image data associated with the key data is retrieved from file devices 1-a to 1-e. The retrieved image data is stored in active files 2-a to 2-f. The image data stored in file devices 2-a to 2-f is erased from file devices 2-a to 2-f.

When arbitrary image data is to be retrieved, key data is supplied from any one of terminals 70-a to 70-c to management device 74. Management device 74 refers to data in the index file based on the key data and retrieves image data associated with the key data from temporary or active file devices 1-a to 1-e or 2-a to 2-f. The retrieved image data is output to a desired one of terminals 70-a to 70-c and is, e.g., displayed. When this image data has been stored in active file devices 2-a to 2-f, it is transferred to temporary file devices 1-a- to 1-e as needed.

For example, the system management device can be arbitrarily distributed by a common data transmission path or a temporary or active file device. In this case, since the index file unit is also distributed, a large scale system can be made easily.

The temporary or active file devices can be distributed in accordance with specific classification, e.g., classification based on the type of the image data. Examples of classification based the type of the image data include those of stored time, key data of an index file, type of data, and identification code.

A database system according to a third embodiment of the present invention will be described with reference to FIG. 7. Temporary and active file devices 1 and 2 similar to those shown in FIG. 2 are provided in the database system of FIG. 7. Transaction file device 80 is provided between file devices 1 and 2. Inactive file device 90 is connected to file device 2. System management device 88 manages file devices 1, 2, 80, and 90.

File device 80 has file control unit 81, memory processing unit 82, memory unit 83, and image retrieval unit 84. Control unit 81 is connected to all of temporary file, active file, and system management devices 1, 2, and 88, and controls file device 80. Memory processing unit 82 is connected to unit 81 and performs processing for storing image data supplied thereto in memory unit 83. Memory unit 83 is connected to both processing and control units 82 and 81 and stores data. Image retrieval unit 84 is connected to both memory and control units 83 and 81, and accesses and reads out data stored in memory unit 83.

Inactive file device 90 has optical disc management unit 91, optical disc carrier unit 92, optical disc access unit 93, and optical disc stock unit 94. Management unit 91 is connected to database system management device 88 and manages handling of optical discs in file device 90. Optical disc carrier unit 92 is connected to management and access units 91 and 93, and active file device 2, and carries optical discs between access unit 93 and file device 2. Access unit 93 is connected to both carrier and optical disc stock units 92 and 94 and takes and returns optical discs out and to stock unit 94. Stock unit 94 stocks optical discs which are used less frequently, and is connected to access and management units 93 and 91.

In the database system having the above arrangement, when image data from image data generator 71 is to be stored, it is first stored in temporary file device 1. Subsequently, after a lapse of a predetermined period of time, the image data is transferred to transaction file control unit 81. Control unit 81 stores the data in memory unit 83 via memory processing unit 82. Memory unit 83 is a rewritable storage and has a memory capacity larger than that of temporary file device 1 and smaller than that of active file device 2. Memory unit 83 is controlled by control unit 81. After a lapse of another predetermined period of time, the image data is read out from memory unit 83 via image retrieval unit 84 under the control of control unit 81, and is transferred to file device 2 via control unit 81. The data is stored in file device 2 for a predetermined period of time, and is then transferred to file device 90.

When the data stored in memory unit 83 is accessed by terminal 70, the accessed data is supplied to terminal 70 and at the same time transferred to and stored in file device 1.

In this manner, since a rewritable storage is divided into a plurality of hierarchical stages and data are stored in different file devices of different stages in accordance with the frequencies they are used, a retrieval time of image data can be shortened.

Data that is stored in active file device 2 exceeding a predetermined period without being accessed is transferred to inactive file device 90. File device 90 is a non-rewritable storage similar to file device 2 and has a memory capacity larger than that of file device 2. Optical disc stock unit 94 of file device 90 stocks a plurality of optical discs that are used comparatively less frequently among those stored in file device 2. Optical discs are taken and returned from and to stock unit 94 by optical disc access unit 93. When data write or read is performed, an optical disc is carried from access unit 93 to file device 2 by optical disc carrier unit 92. The location of the optical disc in file device 90 which stores respective data is managed by optical disc management unit 91.

Optical disc stock unit 94 has 12 disc boxes each having 36 rows × 12 columns of discs. The optical discs are taken out one at a time by access unit 93. Optical discs that are taken out are conveyed to optical disc unit 17 of file device 2. However, discs which are used less frequently by disc unit 17 are conveyed to stock unit 94.

System management device 88 stores file data representing the location of the respective data in file devices 1, 2, 80, and 90. Therefore, when one file device transfers data to another, the filed data is updated.

Figure 7:
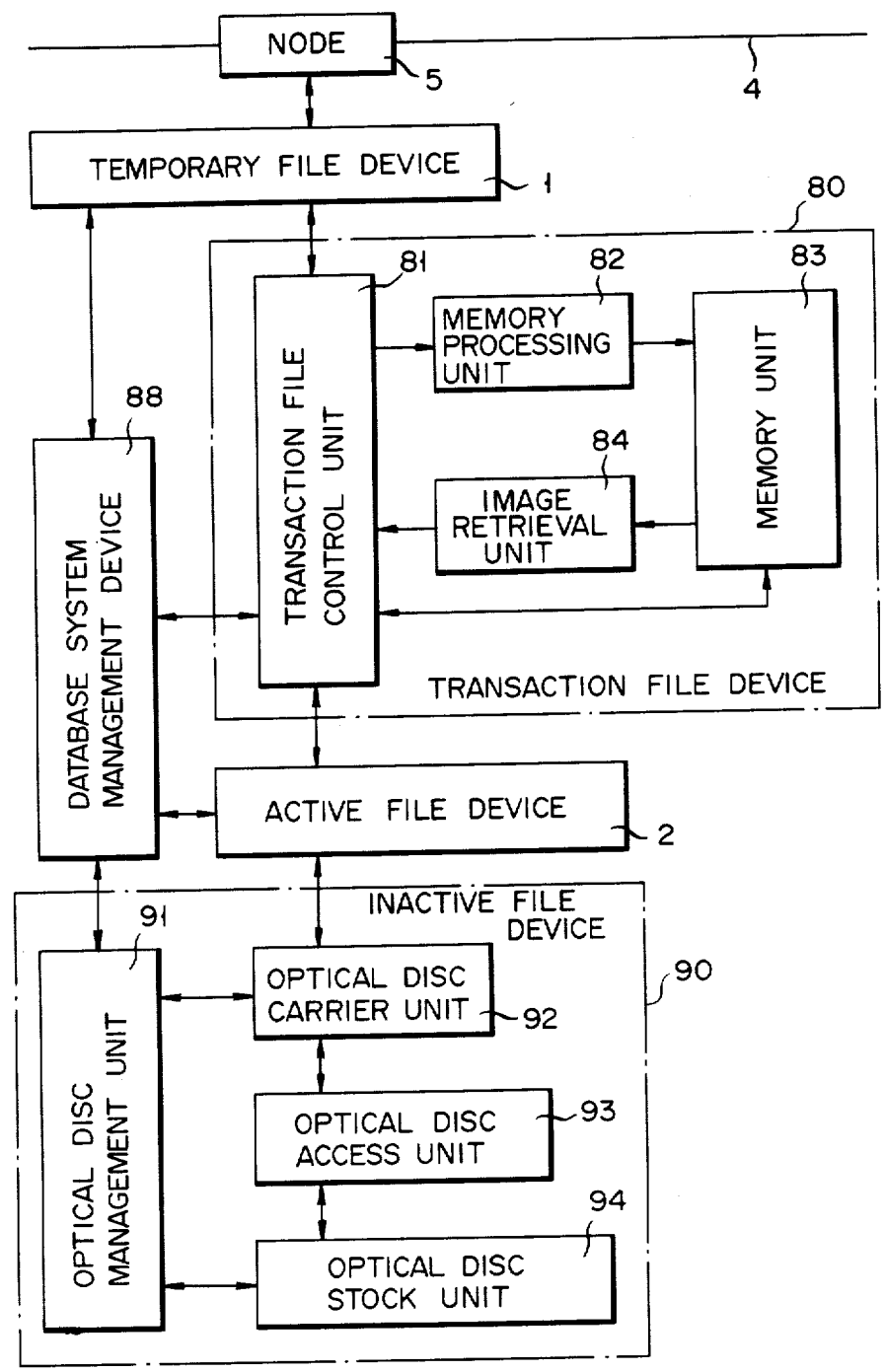
FIG. 7 is a block diagram of a database system according to a third embodiment of the present invention.

The database system according to the third embodiment of the present invention is not limited to the arrangement of FIG. 7 but can be modified in various manners.

For example, the database system can use either transaction file device 80 or inactive file device 90. File devices 80 and 90 can be distributed in the network system.

A database system according to a fourth embodiment of the present invention will be described with reference to FIG. 8. The medical database system shown in FIG. 3 is a database network system for practical use in a hospital.

Figure 8:
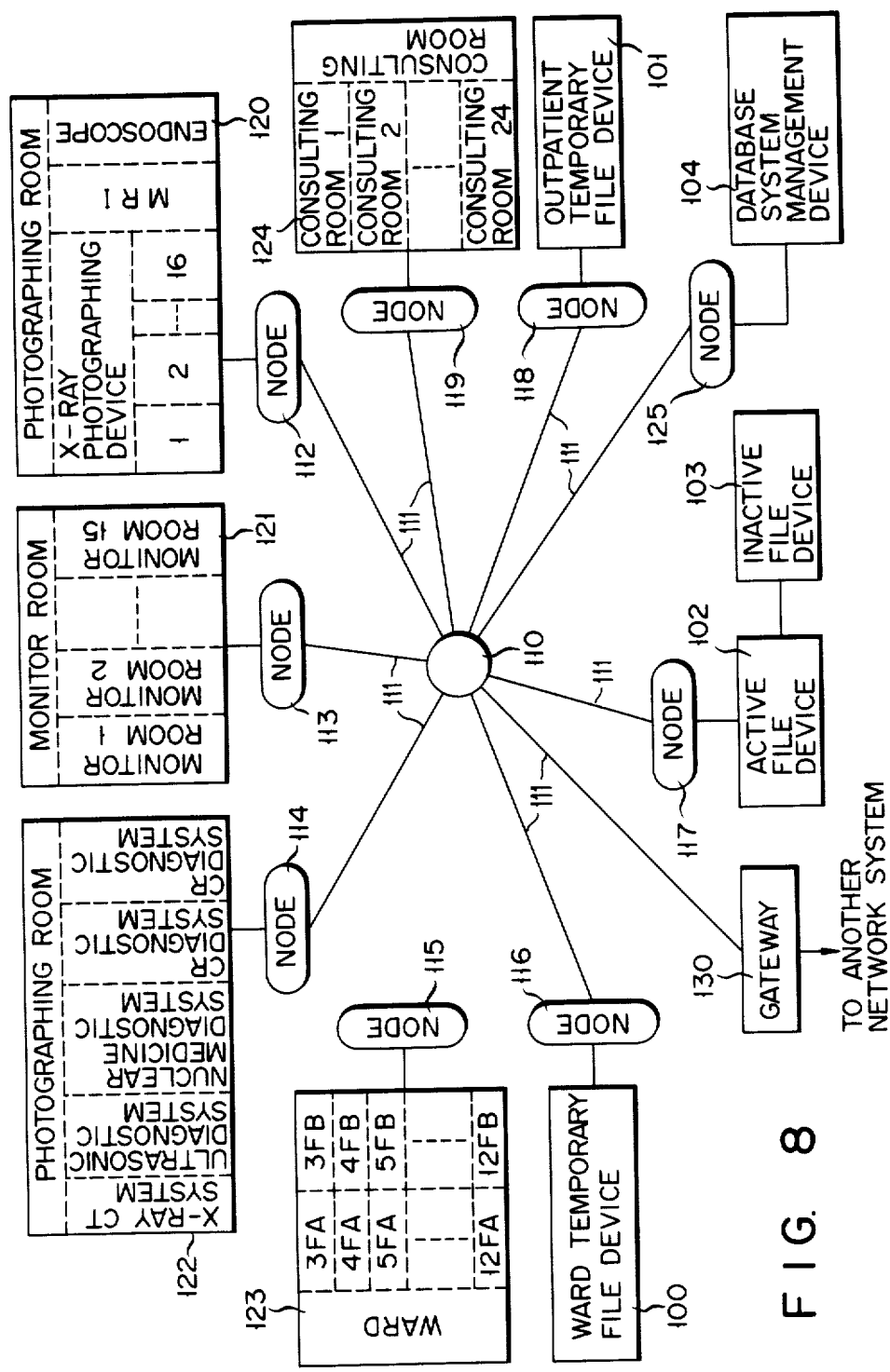
FIG. 8 is a block diagram of a network system including a medical database system according to a fourth embodiment of the present invention.

The network system shown in FIG. 8 has optical star coupler 110, a plurality of fiber cables 111 having one ends connected to coupler 110, nodes 112 to 119 and 125 connected to the other ends of cables 111, and gateway 130. Image data, additional data concerning the image data, retrieval data, and a procedure instruction for arbitrarily exchanging these data in accordance with packet exchange method, are transferred between nodes 112 to 119 and 125 via cables 111 and coupler 110.

Nodes 112 to 119 and 125 are provided in the vicinity of or in photographing room 120, monitor (image determination) room 121, photographing room 122, ward 123, ward temporary file device 100, active file device 102, outpatient temporary file device 101, consulting room 124, and database system management device 104, respectively. Gateway 130 is connected to another network system (e.g., a network system having a database storing clinical chart information) to exchange data with it.

Photographing room 120 has an endoscope system, a magnetic resonance imaging system, and 16 X-ray photographing devices. These systems and devices are connected to node 112 to output image data, additional data concerning the image data (e.g., patient's number, portion under examination, examination method, laboratory number, examination system's name, and examination system's number) through cables 111 as transmission paths.

Photographing room 122 has two computed radiography systems (X-ray photographing diagnostic systems using an imaging plate), a nuclear medicine diagnostic system, an ultrasonic diagnostic system, and an X-ray computed tomography system. These systems are connected to node 114 to output image data, additional data, and so on through it.

Monitor room 121 has 15 subrooms as unit monitor rooms each having a terminal capable of displaying an image. These terminals are connected to node 111 to perform data exchange through it.

Ward 123 has 3 to 6 floor wards A and B each having a terminal. These terminals are connected to node 115.

Consulting room 124 has four subrooms as unit consulting rooms each having a terminal. These terminals ar connected to node 119 to perform data exchange.

The temporary file device is divided into ward and outpatient temporary file devices 100 and 101 connected to nodes 116 and 118, respectively.

Active file device 102 is connected to node 117 and stores data transferred from two file devices 100 and 101.

Inactive file device 103 is connected to file device 102.

System management device 104 is connected to node 125 and manages database file devices 100, 101, 102, and 103.

An example of the operation of the database system which manages data in a hospital will be described below.

FIGS. 9 and 10 show formats of an index file used in this system. Symbols in the lowermost columns of index file 150 mean the types of data stored in the respective items. The data are all fixed-length type data, "9" indicates 1-digit numeral, and "999" indicates 3-digit numeral. "X(12)" indicates 12-digit characters being alphanumeric characters, special characters, or a combination thereof. The other symbols are also based on the same method. Therefore, "XXX" and "X(3)" have the same meaning.

The index file is divided into image address 151 for storing data that roughly indicates the location of image data obtained by one examination, and key data 152 for storing additional data concerning the image data.

Image address 151 consists of file type data 153, file number 154 and address 155. File type data 153 is numerical data indicating file device 100, 102, or 103 that stores predetermined image data. File number 154 is numerical data indicating ward or outpatient temporary file device 100 or 101. Address 155 is a block number (each file device is divided into blocks in units of a predetermined number of image frames) in this case indicating the memory location of the data in a file device.

Key data 152 is also divided into a plurality of items. More specifically, key data 152 includes identification number 156, name 157, sex 158, age 159, and date of birth 160 assigned to each patient, outpatient/inpatient numerical data 161 indicating whether the patient is an outpatient or inpatient, bed data 162 indicating a ward, floor, room, and bed of the inpatient (e.g., bed data "12A07" indicates that the patient is in bed 7 of ward A on 12th floor), image examination date 163, examination portion 164, examination method 165, examination condition 166, laboratory number 167, diagnostic result 168 obtained in accordance with the examination image, reliability 169 of the diagnostic result based on the view of the person in charge of diagnosis, i.e., the doctor, doctor code 170 for identifying the doctor, name 171 of the examination system used for examination, and system number 172.

Address 155 indicates a block location where the image data exists. Therefore, detailed location data in units of images is managed by the file itself.

In the operation of this system, first, image data for diagnosing an outpatient or inpatient and additional data are supplied from a device (devices) in photographing room 120 or 122 to file device 100 or 101 via a network system. In this case, whether the patient is an outpatient or inpatient is determined by system management device 104. If the patient is an outpatient, the above data is transferred to outpatient temporary file device 101. If the patient is an inpatient, the above data is transferred to ward temporary file device 100. Part of key data 152 is transferred to management device 104 almost simultaneously with the transfer of the image data. Key data 152 to be transferred includes patient's number 156, examination date 163, portion 164, method 165, condition 166, laboratory number 167, examination system name 171, and system number 172. The remaining items 157 to 162 in key data 152 can be retrieved from clinical chart data via gateway 130 if patient's number 156 is given. Data corresponding to these items 157 to 162 are retrieved from chart data and input to management device 104. Image address 151 is automatically added in management device 104.

Next, a case will be described wherein image data stored in temporary file device 100 or 101 is retrieved and used for diagnosis in monitor room 121.

Key data is supplied from the terminal provided in monitor room 121 to system management device 104 to obtain a location address or the image, and an instruction requesting readout/transfer of image data is supplied from management device 104 to a device designated by the image data corresponding to the key data. When the address belongs to ward temporary file device 100, image data is transferred from file device 100 to the terminal of monitor room 121. Almost simultaneously, data on the respective items of the key data is supplied from management device 104 to the terminal. The doctor makes diagnosis in accordance with the image data that is retrieved, transferred, and output (displayed) on the terminal, and inputs diagnostic result 168, its reliability 169, and doctor's code 170 from the terminal. In the current state of medical techniques, however, few diseases can be immediately identified based on only several to 20 frames of retrieved images. Normally, in addition to these image data, the patient's clinical data and clinical remarks are retrieved via gateway 130, and diagnosis is performed referring to them.

Among the retrieved image data, those unnecessary for subsequent diagnosis and so on are deleted, and only necessary ones are returned and stored again. In this case, image data can be edited or filtered as required into a form convenient as a reference for diagnosis, and stored thereafter. The image data is transferred to file device 100. The key data is added with diagnostic result 168, reliability 169, and doctor's code 170 and stored in management device 104.

Image data that is not retrieved by monitor room 121, ward 123, or consulting room 124 within a predetermined period (e.g., 3 days) is transferred to active file device 102. In this case, the data at image data address 151 is also updated.

If the data stored in file device 102 is not accessed within a predetermined period (e.g., 40 days), it is further transferred to inactive file device 103.

Image data that is stored in file device 103 and not accessed within a predetermined period (e.g., 3 years) is deleted from the database system or is transferred to another stock unit by the operator's manual operation.

If the data stored in file device 102 is accessed within the predetermined period, it is transferred to either temporary file device 100 or 101 in accordance with the position of the patient (outpatient or inpatient), and almost simultaneously the image data is transferred to a terminal which has sent a retrieval request. In this case, image address 151 is also updated.

Every time patient's data (e.g., outpatient/inpatient, ward, and name) is changed without accessing the image data, new data is supplied from a terminal to system management device 104 and data in device 104 is updated.

In this manner, data on an inpatient or outpatient that is used comparatively frequently is constantly stored in temporary file device 100 or 101, and data which is used frequently next to the above data is stored in active file device 102. Patient's data that is used less frequently is stored in inactive file device 103. The higher the frequency at which image data is used, the shorter the access time of a file device which stores the image data. Therefore, an average access time from a terminal can be shortened.

The present invention can be modified in various manners. For example, file devices 100, 101, 102, and 103 can be distributed in accordance with a classification (e.g., the department of disease such as chest surgery, brain surgery, gastrointernal department, psychiatry, and ophthalmology, or the type of examination systems such as an X-ray CT system, X-ray photographing device, endoscope system, and ultrasonic diagnostic system). Image address 151 of a distributed file device is managed by means of file number 154.

The disease's name to be input from a terminal as diagnostic result 168 is not limited to one; a plurality of diseases' names can be input. In this case, a plurality of reliabilities must be input to correspond to the diseases' names.

A database system according to a fifth embodiment of the present invention will be described with reference to FIG. 11. The system shown in FIG. 11 is obtained by incorporating image compression systems having different compression ratios in temporary and active file devices 1 and 2 of the system shown in FIG. 2.

Figure 11:
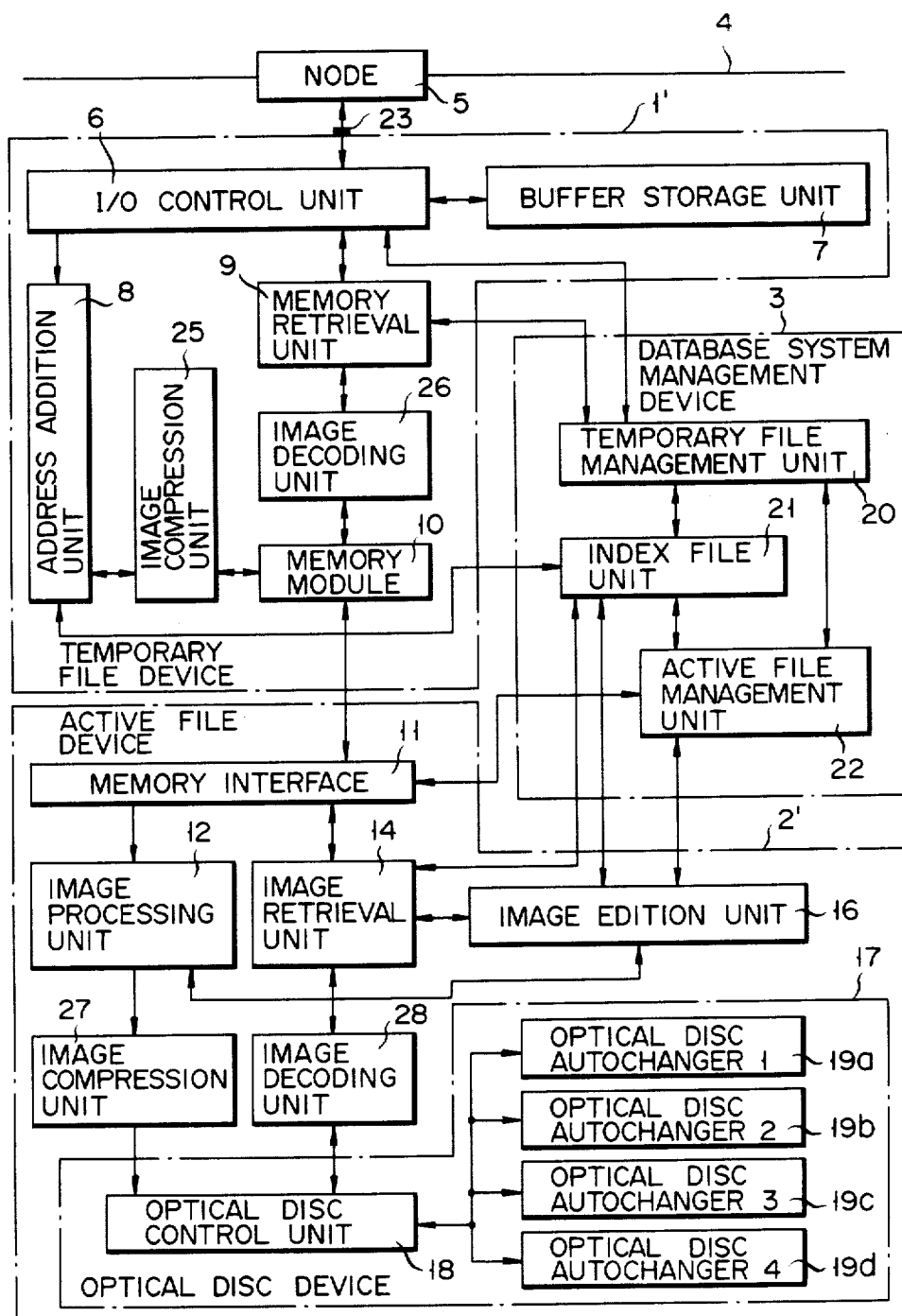
FIG. 11 is a block diagram of a database system according to a fifth embodiment of the present invention.

In temporary file device 1' shown in FIG. 11, image compression unit 25 for compressing image data is provided between address addition unit 8 and memory module 10, and image decoding unit 26 for expanding and hence decoding compressed image data is provided between module 10 and memory retrieval unit 9. When image data is compressed/expanded by compression or decoding unit 25 or 26, a reversible compression method, which has a comparatively low compression ratio but can completely decode original image data from compressed image data, is used. Examples of the compression method of this type include run length coding, Huffman coding, and modified Huffman coding methods. Excluding these points, file device 1' has the same arrangement as file device 1 of FIG. 2.

In temporary file device 2', image compression unit 27 for compressing image data is provided between image processing unit 12 and optical disc control unit 18 of optical disc device 17, and image decoding unit 28 for expanding and hence decoding compressed image data is provided between control unit 18 and image retrieval unit 14. When image data is compressed/expanded by compression or decoding unit 27 or 28, a non-reversible compression method is used which has a comparatively high compression ratio but cannot completely decode original image data from compressed image data, thus degrading the image quality in proportion to an increase in compression ratio. Memory interface 11 is not directly connected to I/O control unit 6 of temporary file device 1' Excluding these points, active file device 1' has the same arrangement as file device 2 of FIG. 2.

The operation of this system is almost the same as that of the system shown in FIG. 2, except for the following points.

More specifically, when image data is to be stored in file device 1', it is compressed by compression unit 25 and stored in memory module 10. When image data is to be read out from file device 1', it is expanded by decoding unit 26 to obtain original image data. Active file device 2' exchanges image data only with module 10 of file device 1'. When image data is to be stored in file device 2', compressed image data which is transferred from module 10 of file device 1' is further compressed by compression unit 27 and is supplied to optical disc device 17. When image data is to be read out from file device 2', compressed image data is expanded by decoding unit 28 to obtain original image data (corresponding to the image data in module 10), and the obtained original image data is transferred to module 10. Therefore, file device 2' stores image data which is compressed at a ratio higher than that stored in file device 1'. Image data read out from file device 2' is further expanded by decoding unit 26 of file device 1' and hence decoded to original image data.

Since this system has different compression ratios for compressing image data to be stored in accordance with the frequency the image data is used, storage efficiency is high. Since the memory capacity is large and recording density is further increased, a substantial memory capacity is considerably increased.

An image compression/decoding unit can be arranged only on either a temporary or active file device.

A database system according to a sixth embodiment of the present invention will be described with reference to FIG. 12. In the system shown in FIG. 12, temporary and active file devices 1 and 2 of FIG. 7 are designed to have the same arrangement as temporary and active file devices 1' and 2' of FIG. 11, and an image compression system is incorporated in transaction file device 80 of the system shown in FIG. 7.

Figure 12:
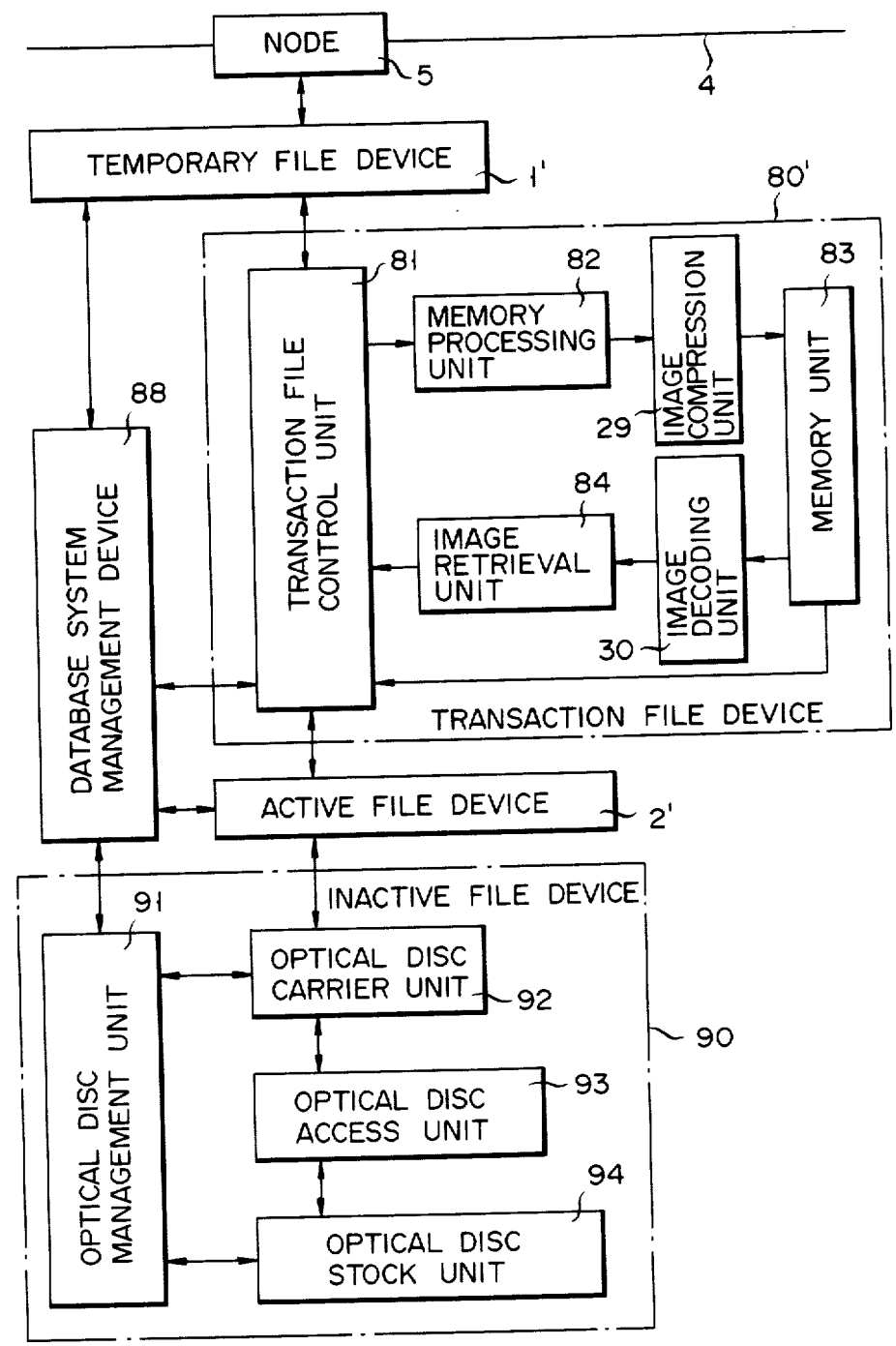
FIG. 12 is a block diagram of a database system according to a sixth embodiment of the present invention.

In transaction file device 80' shown in FIG. 12, image compression unit 29 for compressing image data is provided between memory processing unit 82 and memory unit 83, and image decoding unit 30 for expanding and hence decoding the compressed image data is arranged between memory unit 83 and image retrieval unit 84. When image data is compressed/expanded by compression and decoding units 29 and 30, a reversible compression method is used. Excluding these points, transaction file device 80' has the same arrangement as transaction file device 80 of FIG. 7.

In this case, compression and decoding units 29 and 30 of file device 80' have a compression ratio which is similar to or higher than that of file device 1' and similar to or lower than that of file device 2'.

The operation of this system is almost the same as that of the system shown in FIG. 7, excluding the following points. Namely, in this system when the image data compressed and stored in file device 1' is stored in transaction file device 80', it is compressed further than it is for file device 1'; when the image data compressed and stored in file device 80' is stored in active file device 2', it is compressed further than it is for file device 80'.

As described above, a storage for image data to be stored is divided into a plurality of stages in accordance with the frequency at which the image data is used. Further, the compression ratio for the image data to be stored is also divided into a plurality of stages in accordance with the frequency at which the image data is used, thus further increasing the memory efficiency.

What is claimed is:

1. A database system provided in a network system capable of exchanging data, and capable of storing and retrieving the data via the network system, comprising:
    first data file means, having a rewritable memory unit, for storing data supplied through the network system;
    second data file means, having a memory unit with a larger memory capacity than that of said memory unit of the first data file means, for storing data to be transferred from said first data file means; and
    file management means, for managing the access and storage of data in both said first and second data file means, said file management means being responsive to a utilization characteristic of data stored in said first data file means.

2. A system according to claim 1, wherein:
    said first data file means comprises a plurality of file means that are distributed via the network system.

3. A system according to claim 1, wherein said second data file means comprises a plurality of file means that are distributed via the network system.

4. A system according to claim 1, wherein:
    said second data file means includes file means connected to said first data file means but not through the network system.

5. A system according to claim 2, wherein:
    said plurality of file means are means for storing different types of data that are classified in advance.

6. A system according to claim 21, wherein:

said file management means comprises a plurality of index data memory means distributed on the network system.

7. A system according to claim 6, wherein: said plurality of index data memory means includes rewritable memory means.

8. A system according to claim 1, wherein:
said file management means includes means for directly transferring data read out from said second data file means to said network system.

9. A system according to claim 1, wherein:
said first data file means includes data companding means for compressing and then storing data, and for expanding and outputting readout data, and alternatively said second data file means includes data companding means for compressing and then storing data, and for expanding and outputting readout data.

10. A system according to claim 1, wherein:
said second data file means includes data editing means for editing data stored in said memory unit before it is stored.

11. A system according to claim 1, wherein:
said first data file means includes buffer memory means for temporarily storing data supplied via the network system.

12. A system according to claim 1, wherein:
said file management means includes counter means for counting an elapsed time since data stored in said first data file means is accessed in units of predetermined data groups, and control means for transferring a data group to said second data file means when the elapsed time obtained by said counter means reaches a predetermined value.

13. A system according to claim 1, wherein:
said file management means includes counter means for counting an elapsed time since data stored in said second data file means is accessed in units of predetermined data groups, and control means for deleting a data group from said second data file means when the elapsed time obtained by said counting means reaches a predetermined value.

14. A system according to claim 1, wherein:
said file management means includes control means which, when data stored in said second data file means is accessed, transfers a predetermined data group including the accessed data from said second data file means to first data file means.

15. A system according to claim 1, wherein:
said system further comprises a third data file means, which has a rewritable memory unit having a memory capacity larger than that of said memory unit of the first data file means and smaller than that of said memory unit of the second data file means, for storing data transferred from said first data file means, and said second data file means is a means for storing data transferred from said memory unit of the third data file means.

16. A system according to claim 1, further comprising:
a fourth data file means, which has a non-rewritable memory unit with a memory capacity larger than that of said memory unit of the second data file means, for storing data transferred from said second data file means.

17. A system according to claim 16, wherein:
said memory unit of the second data file means is an optical disc unit having an optical disc as a data recording medium, and said fourth data file means includes a memory unit comprising an optical disc stock unit capable of stocking a plurality of optical discs and carrying means for moving an optical disc between said optical disc stock unit and said optical disc unit.

18. A system according to claim 1, wherein:
said first data file means includes first data companding means for compressing and then storing data, and for expanding data to be read out and then outputting decoded data, and said second data file means includes second data companding means for compressing data with a higher compressing ratio than that of said first companding means and then storing the compressed data, and for expanding data to be read out, and outputting its decoded data.

19. A system according to claim 18, wherein:
said first data companding means is a data companding means capable of completely decoding compressed data, and said second data companding means is a data companding means wherein data decoded thereby is degraded in accordance with a compression ratio thereof.

20. A database system provided in a network system capable of exchanging data, and capable of storing and retrieving the data via the network system, comprising:
first data file means, having a rewritable memory unit, for storing data supplied through the network system;
second data file means, having a memory unit with a larger memory capacity than that of said memory unit of the first data file means, for storing data to be transferred from said first data file means; and
file management means, for managing the access and storage of data in both said first and second data file means, said file management means being responsive to a utilization characteristic of data stored in said first data file means;
a third data file means, which has a rewritable memory unit having a memory capacity larger than that of said memory unit of the first data file means and smaller than that of said memory unit of the second data file means, for storing data transferred from said first file means, and said second data file means is a means for storing data transferred from said memory unit of the third data file means;
a fourth data file means, which has a non-rewritable memory unit with a memory capacity larger than that of said memory unit of the second data file means, for storing data transferred from said second data file means;
said memory unit of the second data file means is an optical disc unit having an optical disc as a data recording medium, and said fourth data file means includes a memory unit comprising an optical disc stock unit capable of stocking a plurality of optical discs and carrying means for moving an optical disc between said optical disc stock unit and said optical disc unit.

21. A database system provided in a network system capable of exchanging data, and capable of storing and retrieving the data via the network system, comprising:
first data file means, having a rewritable memory unit, for storing data supplied through the network system;
second data file means, having a memory unit with a larger memory capacity than that of said memory unit of the first data file means, for storing data to be transferred from said first data file means; and file management means, for managing the access and storage of data in both said first and second data file means, said file management means being responsive to a utilization characteristic of data stored in said first data file means;

said first data file means includes first data companding means for compressing and then storing data, and for expanding data to be read out and then outputting the decoded data, and said second data file means includes second data companding means for compressing data with a higher compressing ratio than that of said first companding means and then storing the compressed data, and for expanding data to be read out, and outputting the decoded data;

said first data companding means is a data companding means capable of completely decoding compressed data, and said second data companding means is a data companding means wherein data decoded thereby is degraded in accordance with a compression ratio thereof.

* * * * *